United States Patent [19]

De et al.

[11] Patent Number: 5,364,637
[45] Date of Patent: Nov. 15, 1994

[54] METHOD AND COMPOSITION FOR CLEANING CONTACT LENSES WITH CYCLODEXTRINS

[75] Inventors: Nimai C. De, Rochester; David J. Heiler, Avon; David A. Marsh; Suzanne F. Groemminger, both of Rochester, all of N.Y.

[73] Assignee: Bausch & Lomb Incorporated, Rochester, N.Y.

[21] Appl. No.: 852,427

[22] Filed: Mar. 16, 1992

Related U.S. Application Data

[63] Continuation of Ser. No. 602,447, Oct. 22, 1990, abandoned.

[51] Int. Cl.$^5$ ............... A61K 9/20; A61K 31/715
[52] U.S. Cl. ................... 424/464; 424/429; 514/839; 514/840
[58] Field of Search ............... 424/464, 427, 429; 514/58, 839, 840

[56] References Cited

U.S. PATENT DOCUMENTS 3,882,036  5/1975  Krezanoski et al. ............... 514/643

Primary Examiner—Thurman K. Page
Assistant Examiner—James M. Spear
Attorney, Agent, or Firm—Craig E. Larson

[57] ABSTRACT

Contact lenses are cleaned by contacting the lenses with a composition containing an effective amount of one or more cyclodextrins. The compositions can also be employed at elevated temperatures or may contain suitable antimicrobial agents in order to simultaneously clean and disinfect the lenses.

10 Claims, No Drawings

METHOD AND COMPOSITION FOR CLEANING CONTACT LENSES WITH CYCLODEXTRINS

This is a continuation of copending application Ser. No. 07/602,447 filed on Oct. 22, 1990, now abandoned.

BACKGROUND OF THE INVENTION

1. Field of the Invention

This invention relates generally to a method and composition for cleaning contact lenses. In one aspect, the present invention relates to a method and composition for cleaning contact lenses with cyclodextrins while in another aspect it relates to a method for simultaneously cleaning and disinfecting contact lenses by contacting the lenses with compositions containing cyclodextrins either under elevated temperatures or in the presence of antimicrobial agents.

2. Description of Art

In the normal course of wearing contact lenses, tear film and debris consisting of proteinaceous, oily, sebaceous, and related organic matter have a tendency to deposit and build up on lens surfaces. As part of the routine and proper care regimen, contact lenses must be cleaned to remove these tear film deposits and debris. If these deposits are not properly removed, both the wettability and optical clarity of the lenses are substantially reduced causing discomfort for the wearer.

Conventionally, the cleaning of contact lenses is accomplished with one or both of two general classes of cleaners. Surfactant cleaners, generally known as "daily cleaners" because of their recommended daily use, are effective for the removal of most carbohydrate and lipid derived matter. However, they are not as effective for the removal of proteinaceous matter such as lysozyme. Proteolytic enzymes derived from plant, animal, and microbial sources are generally used to remove the proteinaceous deposits. These "enzyme" cleaners are typically recommended for weekly use and are conventionally employed by dissolving enzyme-containing tablets in suitable solutions. Both cleaners are currently recommended for proper care of contact lenses, particularly those made from hydrophilic materials.

Cyclodextrins have been known for nearly a century being first isolated from the degradation products of starch. They are cyclic oligosaccharides produced by the enzymatic degradation of starch. The degradation enzymes used are typically produced by various microorganisms such as bacilli. Generally, cyclodextrins have been commercially employed in the pharmaceutical industry as inclusion or entrapment agents for the purpose of solubilizing relatively insoluble compounds preventing the evaporation of volatile compounds stabilizing volatile or heat labile compounds, enhancing the bioavailability of certain drugs and related purposes. Hence, conventional uses of cyclodextrins involve the inclusion of an active compound into the cyclodextrin molecular structure prior to use and employ the cyclodextrin as a means for delivering the active compound.

It has now been found that cyclodextrin compositions can be employed under ambient and elevated temperatures to remove many of the deposits, which adhere to contact lenses during normal wear including, proteinaceous matter, typically the most difficult deposits to remove. These compositions contain cyclodextrins which do not contain active compounds incorporated into the cavity of the cyclodextrin. Moreover, it has been surprisingly found that the continued and regular use of cyclodextrin cleaning compositions result in an effective technique for preventing proteinaceous deposit build-up on contact lenses.

SUMMARY OF THE INVENTION

According to this invention, a method for cleaning contact lenses is provided comprising contacting the lenses with a composition containing from 0.0001% to about 10% by weight of one or more cyclodextrins for a time sufficient to clean the lenses. A contact lens cleaning composition is also provided comprising from 0.0001% to about 10% by weight of one or more cyclodextrins.

Also provided herein is a method for simultaneously cleaning and disinfecting contact lenses comprising contacting the lenses with a composition containing from 0.0001% to about 10% by weight of one or more cyclodextrins at a temperature of at least about 60° C. for a time sufficient to clean and disinfect the lenses.

Yet another method is provided herein for simultaneously cleaning and disinfecting contact lenses comprising contacting the lenses with a composition containing from 0.0001% to about 10% by weight of one or more cyclodextrins and a disinfecting amount of an antimicrobial agent for a time sufficient to clean and disinfect the lenses.

DETAILED DESCRIPTION OF THE INVENTION

The present invention can be used with all contact lenses such as conventional hard, soft, rigid gas permeable, and silicone lenses but is preferably employed with soft lenses such as those commonly referred to as hydrogel lenses prepared from monomers such as hydroxyethylmethacrylate, vinylpyrrolidone, glycerol-methacrylate, methacrylic acid or acid esters and the like. Hydrogel lenses typically absorb significant amounts of water such as from 4 to 80 percent by weight.

The compositions employed herein contain at least one or more cyclodextrins in a suitable carrier. Other active or inactive components can also be employed in the cleaning compositions.

As described above, the cyclodextrins used in the present invention are cyclic oligosaccharides produced by the enzymatic degradation of starch and have multiple glucose or glucopyranose units, usually 6 to 8 units. Depending on the particular preparation reaction conditions employed, cyclodextrins generally contain six, seven or eight of such units, connected by alpha-(1,4) bonds. The six, seven or eight unit cyclodextrins are commonly known as alpha-, beta-, and gamma-cyclodextrins, respectively.

Cyclodextrins have the shape of truncated cones with primary and secondary hydroxyl groups located at opposite ends of the torus. The glucosyl-o-bridges point into the center of the molecule and the primary hydrogel groups project from one outer edge while the secondary hydroxyl groups project from the other edge. The result is a molecule with a relatively hydrophobic center and a hydrophilic outer surface. These shapes and hydrophilic/hydrophobic domains provide for inclusion or incorporation of guest molecules into the center of the molecule.

Cyclodextrins are well known and are commercially produced by the enzymatic degradation of starch. For example, beta-cyclodextrin is the major product of the reaction between the enzyme cyclodextrin transglycosylase and a starch solution pretreated with gamma-amylase.

As used herein, the term "cyclodextrins" includes all cyclodextrin derivatives, such as cyclodextrin carbonates, ethers, esters, and polyethers; polymers or copolymers of polymerized cyclodextrins, such as polymerized beta-cyclodextrins; and substituted cyclodextrins such as those with functional groups bonded to one or more of the hydroxyl groups. Suitable function groups include, but are not limited to, methyl, ethyl, hydroxyethyl, and hydroxypropyl and acetyl groups. The cyclodextrin derivatives can also include cyclodextrins with functional groups replacing one or more of the hydroxyl groups such as amino-cyclodextrin, iodo-cyclodextrin and cyclodextrin sulfate. Some of these functional groups may also contribute preserving or disinfecting properties.

The preferred cyclodextrins are the beta-cyclodextrins and most preferred are beta-cyclodextrin selected from beta-cyclodextrin, hydroxypropyl beta-cyclodextrin, methyl beta-cyclodextrin and hydroxyethyl beta-cyclodextrin when the cyclodextrin compositions are employed at elevated temperatures.

The present invention employs an effective amount of cyclodextrin to clean the lenses. An effective amount is that required to remove a substantial portion of the proteinaceous deposits, which occur during normal wear of contact lenses, in a reasonable time. The precise amount of cyclodextrin required to make an effective cleaner will depend on several factors including the type of cyclodextrin, the amount of proteinaceous matter deposited on the lenses, the desired soaking period, the specific type of materials comprising the lenses, and the like. Further, it should be appreciated by one skilled in the art, that the cyclodextrin concentrations useful herein will be adjusted depending upon the time allowed for removing the proteinaceous matter, the other components in the composition and the factors previously mentioned. However, cyclodextrins will generally be present in an amount from 0.0001% to about 10% by weight with from about 0.01% to about 2.0% being preferred.

The compositions of the present invention may contain various additional components which do not adversely affect, to any significant extent, the activity of the cyclodextrins. Illustrative examples of components which may be found in the composition include one or more of a suitable antimicrobial agent, buffering agent, chelating and/or sequestering agent, a tonicity adjusting agent, and surfactant.

The cyclodextrin composition may contain a preserving or disinfecting amount of one or more antimicrobial agents which are compatible with and do not adversely affect the activity of the cyclodextrins or other components. Suitable chemical antimicrobial agents, as the term is used herein, include quaternary ammonium salts and polymers used in ophthalmic applications such as poly[(dimethyliminio)-2-butene-1,4-diyl chloride], [4-tris(2-hydroxyethyl) ammonio]-2-butenyl-W-[tris(2-hydroxyethyl) ammonio]dichloride (chemical registry number 75345-27-6) generally available as polyquaternium $1^R$ from ONYX Corporation; benzalkonium halides; trialkylammonium halides; biguanides such as salts of alexidine, alexidine free base, salts of chlorhexidine, hexamethylene biguanides and their polymers; and the like. The salts of alexidine and chlorhexidine can be either organic or inorganic and are typically gluconates, nitrates, acetates, phosphates, sulfates, halides and the like.

Suitable oxidative antimicrobial agents, as the term is used herein, include any peroxide sources which produce active oxygen in solution and any iodine liberating sources which produce preserving or disinfecting amounts of iodine compounds in solution. Examples of such agents include hydrogen peroxide and its alkali metal salts; alkali metal perborates and persulfates; alkali metal carbonate peroxide; diperisophthalic acid; peroxydiphosphate salts; sodium aluminium aminohydroperoxide; iodine and iodophors. Preferred oxidative antimicrobial agents are peroxides and iodophors.

The antimicrobial agents can also be employed after the cleaning step using the cyclodextrin composition. In this application, the cleaning step would be followed with a disinfecting step in a conventional regimen.

A preserving amount of an antimicrobial agent is an amount which will substantially inhibit the microorganism population from growing while a disinfecting amount is an amount which will reduce the microorganism population. Preferably, a preserving amount of antimicrobial agent will substantially inhibit the microorganism population growth for at least thirty (30) days after exposure to environmental air. Preferably, a disinfecting amount of an antimicrobial agent is that which will reduce the microbial burden by about two log orders in four hours and, more preferably, by about one log order in one hour. Typically, such agents are present in concentrations ranging from about 0.00001% to about 0.5% (w/v), and more preferably, from about 0.00003% to about 0.05% (w/v).

The compositions of the present invention can be prepared in various physical forms such as liquids, solids, emulsions or colloidal suspensions. For example, the cyclodextrins and additional ingredients can be dissolved or suspended in a suitable solvent such as water, glycerol, propylene glycol and the like. Alternatively, the composition can be in the form of a powder or tablet wherein the latter will typically contain binders or other excipients commonly used in the tableting industry. Further, the cyclodextrins can be incorporated into liposomes, microsponges, microspheres and other drug delivery systems.

Rather than including a disinfecting amount of an antimicrobial agent into the present composition, the cleaning composition can also be formulated for use in a contact lens heat disinfecting apparatus. Such devices are well known and are commercially available through numerous companies. These devices typically raise the temperature of the composition inside their wells to between about 60° C. and 100° C. for about 20 to 60 minutes as required to disinfect the lenses.

During the normal practice of one embodiment of the present invention, soiled lenses are placed in the cleaning composition for a period of about 15 minutes to about 12 hours either with or without a prior rubbing (as is currently recommended for daily cleaners). After soaking the lenses for the appropriate time, the lenses are removed and disinfected using conventional techniques such as elevated temperatures or disinfecting solutions.

In another embodiment of the invention, the composition can contain an effective amount of an antimicrobial agent. The composition can then be employed to simultaneously clean and disinfect the lenses during the required soaking period. In the case of oxidative antimicrobial agents, the residual agent remaining on the lenses must be neutralized prior to placing the lenses in the eye. Such neutralizing agents and methods are well known in the art. In the case of chemical antimicrobial agents, a neutralization step is generally not required.

In a preferred embodiment of the invention, the cleaning composition is placed in a contact lenses heat disinfecting unit which is capable of raising the temperature of the composition to at least 60° C. for at least about 10 minutes or as otherwise necessary to disinfect the lenses. The soiled contact lenses are then placed in the cleaning composition within the unit for a time sufficient to clean and disinfect the lenses. Typically, the cleaning and disinfecting process will take less than about 60 minutes depending on the specific unit employed and is typically about 15 to about 40 minutes. Conventional heat disinfecting units already known to disinfect contact lenses are suitable for use with the cyclodextrin composition to achieve cleaning and disinfection. Advantageously, the lenses can be removed from the solution and placed directly into the eye without the need for a separate disinfecting or neutralizing step. Optionally, the lenses may be rinsed with a suitable isotonic aqueous solution prior to insertion into the eye.

The following detailed examples are presented to illustrate the present invention. Both ambient and thermal (elevated temperatures) cleaning efficacy were performed using protein deposited Group IV contact lenses and cyclodextrin compositions. All percentages below are by weight.

Group IV (etafilcon 58% water) lenses were deposited by soaking each lens for 18 hours at 37° C. (approximate corneal temperature). The soaking solution consisted of four major tear proteins: lysozyme, albumin, lactoferrin, and mucin; and electrolytes, all in concentrations reportedly found in human tears. The final soaking solution contained 0.1% mucin, 0.17% lysozyme, 0.05% lactoferrin, 0.085% albumin, 0.7% sodium chloride, 0.005% calcium chloride, and 0.05% sodium phosphate dibasic. The remainder of the soaking solution comprised deionized and distilled water with the pH adjusted to 7.2 with 1N hydrochloric acid. After soaking for 18 hours each lens was rubbed and rinsed lightly with isotonic saline to remove non-bound protein solution.

Each of the cyclodextrin compositions were prepared by mixing 1.0% of the selected cyclodextrin in an aqueous isotonic phosphate buffered saline containing 0.3% hydrated sodium phosphate dibasic, and 0.9% sodium chloride. The remainder of the solution was deionized, distilled water with the pH adjusted to 7.2 with 1N hydrochloric acid.

Example 1

Ten protein deposited lenses were allowed to soak in 10 ml per lens of the cyclodextrin composition. After 4 hours, the lenses were removed from the test solution and soaked in the isotonic phosphate buffered saline for about 10 minutes to remove excess solution. The lenses were analyzed to determine the total remaining protein bound to the lens after cleaning using a standard ninhydrin assay for the colorimetric determination of protein adapted for use with hydrophilic contact lenses.

The ninhydrin reagent was prepared according to the method described by Shibata and Matoba in *Modified Colorimetric Ninhydrin Methods for Peptidase Assay,* Analytical Biochemistry 1981; 118:173–184. A citrate-acetate buffer was prepared with 0.5 moles acetic acid and 0.1 moles citric acid adjusted to pH 5.0 with 10N sodium hydroxide. The ninhydrin reagent was prepared by dissolving 20 mg of stannous chloride and 200 mg of ninhydrin in 10 ml of methyl cellosolve (ethylene glycol, monomethyl ether), then adding 10 ml of the citrate-acetate buffer.

The protein bound to the lenses was hydrolyzed to their amino acid components by heating the lenses in 1 ml of 2.5N NaCl for 2 hours at 100° C. Aliquots of hydrolyzed solution samples (0.015 ml) were placed into disposable polystyrene culture tubes. The samples were diluted with 2.5N sodium hydroxide prior to performing the analysis. To neutralize the sodium hydroxide, glacial acetic acid (0.050 ml) was added to each of the culture tubes and the tubes were vortexed. Ninhydrin reagent (0.40 ml) was added to each tube, followed by vortexing.

The polystyrene tubes were capped and heated in a water bath at 90° C. for 20 minutes, during which time color development occurred. After 20 minutes, samples were transferred to an ice bath and diluted with 1.0 ml of 50% aqueous 2-propanol.

The absorbance of each sample was recorded at 570 nm on a Spectophotometer. Standard protein calibration curves (absorbance vs protein concentration) were prepared in the 0.0–15.0 ug range with a known amount of a lysozyme standard subjected to the same analysis procedure. A protein standard was prepared using lysozyme (Grade I, from chicken egg white, 3× crystallized, dialyzed and lyophilized; Sigma Chemical Company). A known amount of lysozyme was added to a culture tube and dissolved in 1.0 ml of 2.5N sodium hydroxide. The culture tubes containing the lenses and the lysozyme standard were tightly capped and placed into a heating block preheated to 100° C. Samples were hydrolyzed for two hours, removed from the heating block and allowed to cool to room temperature.

Protein concentrations were determined by comparison of absorbance readings with the lysozyme standard curve and calculating the concentration of protein per lens based on appropriate dilution factors. The results are shown in Table 1.

Example 2

Protein deposited lenses were placed into a Bausch & Lomb White Lens Carrying Case containing 3 ml of the cyclodextrin composition. The lens cases were cycled through one disinfecting cycle in a Bausch & Lomb DUIV Thermal Disinfecting Unit. The typical heat profile of this unit raises the solution temperature to greater than 60° C. for about 20 minutes, and greater than 70° C. for about 10 minutes. This heat profile is commonly accepted as that necessary to disinfect contact lenses. After the cycle was complete, each lens was soaked in an isotonic phosphate buffered saline solution to remove any residual cyclodextrin composition adhering to the lenses prior to total protein analysis by a similar procedure as described in Example 1.

Control protein levels were established for the lenses by using 10 lenses which have had protein deposited on them using the procedure described above and which have not been previously cleaned. The percent cleaning was determined by subtracting the tested values from the control values and dividing by the control values. This number is multiplied by 100 to convert to percent. The results are shown in Table 1.

As shown in Table 1, the cyclodextrin composition exhibited cleaning activity under both ambient and elevated temperatures.

Thus, it should be apparent to those skilled in the art that the present invention is not limited by the examples set forth above and that the use of specific compositions can be determined from the specification without departing from the invention as herein disclosed and described. It should be understood that the scope of the present invention includes all modifications and variations that fall within the scope of the attached claims.

TABLE 1

Ambient and Thermal Cleaning of Contact Lenses

| Compound* | Average Protein Remaining on Lens (micro grams) | Standard Deviation (N = 10) | | Percent Cleaning |
|---|---|---|---|---|
| Example 1 (Ambient) | | | | |
| Control | 1115.1 | +/− | 73.5 | |
| Alpha-Cyclodextrin | 891.5 | +/− | 111.2 | 20.0 |
| Gamma-Cyclodextrin | 934.8 | +/− | 73.1 | 16.1 |
| Beta-Cyclodextrin | 993.0 | +/− | 69.1 | 10.9 |
| Methyl-Beta-Cyclodextrin | 1042.8 | +/− | 46.0 | 6.5 |
| Hydroxypropyl-Beta-Cyclodextrin MS = 0.6 | 1079.4 | +/− | 105.2 | 3.2 |
| Hydroxyethyl-Beta-Cyclodextrin MS = 0.6 | 1127.6 | +/− | 120.7 | −1.0 |
| Example 2 (Thermal) | | | | |
| Control | 1115.1 | +/− | 73.5 | |
| Alpha-Cyclodextrin | 939.0 | +/− | 106.9 | 15.8 |
| Gamma-Cyclodextrin | 991.1 | +/− | 76.4 | 11.1 |
| Beta-Cyclodextrin | 925.7 | +/− | 71.2 | 17.0 |
| Methyl-Beta-Cyclodextrin | 860.1 | +/− | 65.3 | 27.9 |
| Hydroxypropyl-Beta-Cyclodextrin MS = 0.6 | 826.5 | +/− | 15.8 | 25.9 |
| Hydroxyethyl-Beta-Cyclodextrin MS = 0.6 | 908.5 | +/− | 24.6 | 18.5 |

What is claimed:

1. A method for cleaning contact lenses of organic, proteinaceous matter comprising contacting the lenses with a composition containing as a cleaning agent one or more cyclodextrins selected from the group consisting of alpha-cyclodextrins, beta-cyclodextrins and gamma-cyclodextrins for a time sufficient to clean the lenses, wherein said cleaning agent is present in an effective amount of about 0.0001% to about 10% by weight of said composition.

2. The method of claim 1 wherein the composition is in the form of a tablet dissolved in a solvent.

3. A method for simultaneously cleaning contact lenses of organic, proteinaceous matter and disinfecting said contact lenses, comprising:
   contacting the lenses with an aqueous composition containing as a cleaning agent an effective amount of one or more cyclodextrins selected from the group consisting of beta-cyclodextrin, hydroxypropyl beta-cyclodextrin, methyl beta-cyclodextrin, and hydroxyethyl beta-cyclodextrin for cleaning the lenses of said organic proteinaceous matter, wherein said effective amount is about 0.01% to about 2.0% by weight of said composition; and
   simultaneously elevating said lenses and composition to a temperature of at least about 60° C. for a time sufficient to disinfect the lenses.

4. The method of claim 3 wherein the temperature is at least 60° C. for at least about 10 minutes.

5. The method of claim 3 wherein the composition is in the form of a tablet dissolved in a solvent.

6. A method for simultaneously cleaning contact lenses of organic, proteinaceous matter and disinfecting said contact lenses, comprising: contacting the lenses with
   (a) an aqueous composition containing as a cleaning agent an effective amount of about 0.0001% to about 10.0% by weight of one or more cyclodextrins, and
   (b) a disinfecting amount of an antimicrobial agent for a time sufficient to clean and disinfect the lenses, wherein said antimicrobial agent differs from said cyclodextrins or complexes thereof.

7. The method of claim 6 wherein the cyclodextrin is a beta-cyclodextrin in an amount from about 0.01% to about 2.0% by weight.

8. A method for preventing proteinaceous deposit build-up on contact lenses comprising contacting the lenses in accord with the methods of claim 1 or 3.

9. A method of using one or more cyclodextrins, in an effective amount of about 0.0001% to about 10.0% by weight of an aqueous composition of said cyclodextrins for cleaning organic matter from contact lenses.

10. A method for cleaning contact lenses of proteinaceous matter, comprising contacting the lenses with a cleaning composition consisting essentially of an effective amount of one or more cyclodextrins for a time sufficient to clean the lenses, wherein said effective amount is about 0.01% to about 2.0% by weight of said composition.

* * * * *